United States Patent
Shim

(10) Patent No.: US 11,730,894 B2
(45) Date of Patent: Aug. 22, 2023

(54) TIP FOR INTRA-TYMPANIC INJECTION

(71) Applicant: Min Bo Shim, Seoul (KR)

(72) Inventor: Min Bo Shim, Seoul (KR)

(*) Notice: Subject to any disclaimer, the term of this patent is extended or adjusted under 35 U.S.C. 154(b) by 506 days.

(21) Appl. No.: 16/632,822

(22) PCT Filed: Jul. 20, 2018

(86) PCT No.: PCT/KR2018/008203
§ 371 (c)(1),
(2) Date: Jan. 21, 2020

(87) PCT Pub. No.: WO2019/017721
PCT Pub. Date: Jan. 24, 2019

(65) Prior Publication Data
US 2021/0128843 A1    May 6, 2021

(30) Foreign Application Priority Data

Jul. 21, 2017 (KR) ......................... 10-2017-0092742
Jul. 19, 2018 (KR) ......................... 10-2018-0084286

(51) Int. Cl.
*A61M 5/32* (2006.01)

(52) U.S. Cl.
CPC ... *A61M 5/3287* (2013.01); *A61M 2210/0662* (2013.01)

(58) Field of Classification Search
CPC .................. A61M 5/31; A61M 5/3287; A61M 2210/0662; A61M 2210/0068; A61M 2205/3289; A61M 2210/0668; A61F 11/202; A61F 11/20
See application file for complete search history.

(56) References Cited

U.S. PATENT DOCUMENTS

| | | | | |
|---|---|---|---|---|
| 2,879,768 A | * | 3/1959 | Algot ................. | A61M 3/0283 604/39 |
| 3,675,641 A | * | 7/1972 | Fiore .................. | A61B 1/32 600/184 |
| 3,848,587 A | * | 11/1974 | McDonald ............ | A61B 1/07 600/187 |
| 3,870,036 A | * | 3/1975 | Fiore .................. | A61B 1/31 600/184 |
| 3,878,836 A | * | 4/1975 | Twentier ............. | A61B 1/00142 374/E1.013 |
| 3,949,740 A | * | 4/1976 | Twentier ............. | A61B 1/00142 374/E1.013 |
| 4,258,714 A | * | 3/1981 | Leopoldi ............. | A61M 3/0262 D24/115 |

(Continued)

FOREIGN PATENT DOCUMENTS

JP     2010-524584 A     7/2010
KR  10-2010-0130765 A    12/2010

(Continued)

*Primary Examiner* — Nathan R Price
*Assistant Examiner* — Mark A Igel
(74) *Attorney, Agent, or Firm* — NKL Law; Jae Youn Kim

(57) ABSTRACT

Provided is a tip for intra-tympanic injection capable of allowing a practitioner to accurately recognize an injection location and preventing the practitioner from piercing regions of an external auditory meatus other than the eardrum with an injection needle, in case of piercing the eardrum with the injection needle.

12 Claims, 18 Drawing Sheets

(56) References Cited

U.S. PATENT DOCUMENTS

| | | | | |
|---|---|---|---|---|
| 4,766,886 A | * | 8/1988 | Juhn | A61F 11/202 600/200 |
| 4,895,164 A | * | 1/1990 | Wood | G01J 5/049 374/126 |
| 5,364,343 A | * | 11/1994 | Apolet | A61M 3/0283 604/35 |
| 5,665,094 A | * | 9/1997 | Goldenberg | A61M 1/84 604/212 |
| 5,916,150 A | * | 6/1999 | Sillman | A61B 10/06 600/184 |
| 6,152,873 A | * | 11/2000 | Rogers | A61B 1/227 600/187 |
| 6,432,045 B2 | * | 8/2002 | Lemperle | A61B 1/32 600/210 |
| 6,706,023 B1 | * | 3/2004 | Huttner | A61M 3/0283 604/264 |
| 8,062,216 B2 | * | 11/2011 | Raghuprasad | A61B 1/227 604/257 |
| 8,131,380 B2 | * | 3/2012 | Cao | A61B 1/31 606/41 |
| 8,459,844 B2 | * | 6/2013 | Lia | A61B 1/06 362/326 |
| 10,994,069 B1 | * | 5/2021 | Jiang | A61M 3/0262 |
| 2006/0095066 A1 | * | 5/2006 | Chang | A61M 25/10 606/199 |
| 2006/0142736 A1 | * | 6/2006 | Hissink | A61L 29/148 424/422 |
| 2006/0253087 A1 | * | 11/2006 | Vlodaver | A61M 3/0287 604/212 |
| 2008/0262468 A1 | * | 10/2008 | Clifford | A61M 31/00 604/501 |
| 2011/0301572 A1 | * | 12/2011 | Vlodaver | A61F 11/00 604/246 |
| 2012/0203200 A1 | * | 8/2012 | Kenney | A61F 11/00 604/60 |
| 2012/0296268 A1 | * | 11/2012 | Vlodaver | A61M 31/00 604/43 |
| 2013/0338568 A1 | * | 12/2013 | Mehta | A61M 3/0287 604/19 |
| 2014/0031852 A1 | * | 1/2014 | Edgren | A61B 17/24 606/199 |
| 2015/0003644 A1 | * | 1/2015 | George | A61H 21/00 381/165 |
| 2015/0119856 A1 | * | 4/2015 | Vlodaver | A61M 3/0262 604/514 |
| 2015/0217089 A1 | * | 8/2015 | Chuang | A61M 5/3287 604/506 |
| 2016/0250456 A1 | * | 9/2016 | Vlodaver | A61M 31/00 604/212 |
| 2016/0361078 A1 | * | 12/2016 | Pagliacci | A61M 1/84 |
| 2017/0340485 A1 | * | 11/2017 | Verhoeven | A61F 11/00 |
| 2019/0046233 A1 | * | 2/2019 | Feng | A61B 17/3403 |
| 2020/0078509 A1 | * | 3/2020 | Bryning | A61M 3/0208 |
| 2020/0094030 A1 | * | 3/2020 | Kim | A61B 1/00066 |
| 2021/0023280 A1 | * | 1/2021 | Stanley | A61M 3/0262 |
| 2021/0059859 A1 | * | 3/2021 | O'Shea | A61B 17/3421 |

FOREIGN PATENT DOCUMENTS

| | | | | |
|---|---|---|---|---|
| KR | 10-2012-0115739 A | 10/2012 | | |
| KR | 10-1260676 B1 | 5/2013 | | |
| KR | 10-2015-0095629 A | 8/2015 | | |
| WO | WO-9742921 A1 | * | 11/1997 | A61B 1/227 |
| WO | WO-2010122537 A1 | * | 10/2010 | A61M 3/0262 |

* cited by examiner

TIP FOR INTRA-TYMPANIC INJECTION

TECHNICAL FIELD

The disclosure relates to a tip for intra-tympanic injection.

BACKGROUND ART

In case of performing a surgery, such as an injection of drugs and/or blood directly into a tympanum, a practitioner needs to insert an injection needle into an eardrum.

Since such a surgery requires accurate insertion of an injection needle to an eardrum, the movement of a patient needs to be minimized during the surgery, and very high level of skill is demanded to a practitioner.

When a practitioner is inexperienced or a patient moves during a surgery, an injection needle may not be correctly inserted to an eardrum and pierce an external auditory meatus around the eardrum or the practitioner may inject a drug into the external auditory meatus without penetrating through the eardrum with the injection needle.

Furthermore, once blood is injected beyond an eardrum, the blood may partially fill an external auditory meatus, and thus even an experienced practitioner may be unable to visually recognize the eardrum when performing a surgery again after a certain time.

DESCRIPTION OF EMBODIMENTS

Technical Problem

The disclosure provides a tip for intra-tympanic injection that enables a practitioner to easily insert an injection needle at a correct location of an eardrum.

Solution to Problem

According to an aspect of the disclosure, there is provided a tip for intra-tympanic injection, the tip including a body provided with a first end portion having a smaller cross-section than a second end portion for insertion into an external auditory meatus; a first opening located at a first end portion of the body; a second opening located at a second end portion of the body; and a communicating path configured to penetrate through the body to connect the first opening and the second opening.

The body may include an outer casing and a filled portion, which is located inside the outer casing and provided with the communicating path.

The outer casing may be provided to have elasticity.

The filled portion may include a harder material than the outer casing.

The tip may further include a handle located outside the second end portion of the body.

According to another aspect of the disclosure, there is provided a tip for intra-tympanic injection, the tip including a second tip configured to be inserted into an external auditory meatus; and a first tip configured to be inserted to the second tip, wherein the first tip includes a body, which is at least partially in close contact with an inner surface of the second tip; and a communicating path configured to penetrate through the body and at least partially including a linear portion.

The communicating path may include a first communicating path adjacent the first opening; and a second communicating path connected to the first communicating path and adjacent to the second opening, and a diameter of at least a portion of the second communicating path is greater than a diameter of the first communicating path.

The body may be provided with a curved surface from the first end portion toward the second end portion.

A diameter of the first opening may be smaller than a diameter of the second opening.

The communicating path may include a portion provided in a linear shape.

Advantageous Effects of Disclosure

When a practitioner pierces an eardrum with an injection needle, the practitioner may accurately recognize an injection location.

Also, the disclosure may prevent the practitioner from piercing regions of an external auditory meatus other than the eardrum with the injection needle.

The disclosure may improve the accuracy of a surgery and reduce discomfort and pain of a patient.

MODE OF DISCLOSURE

Figure 1:
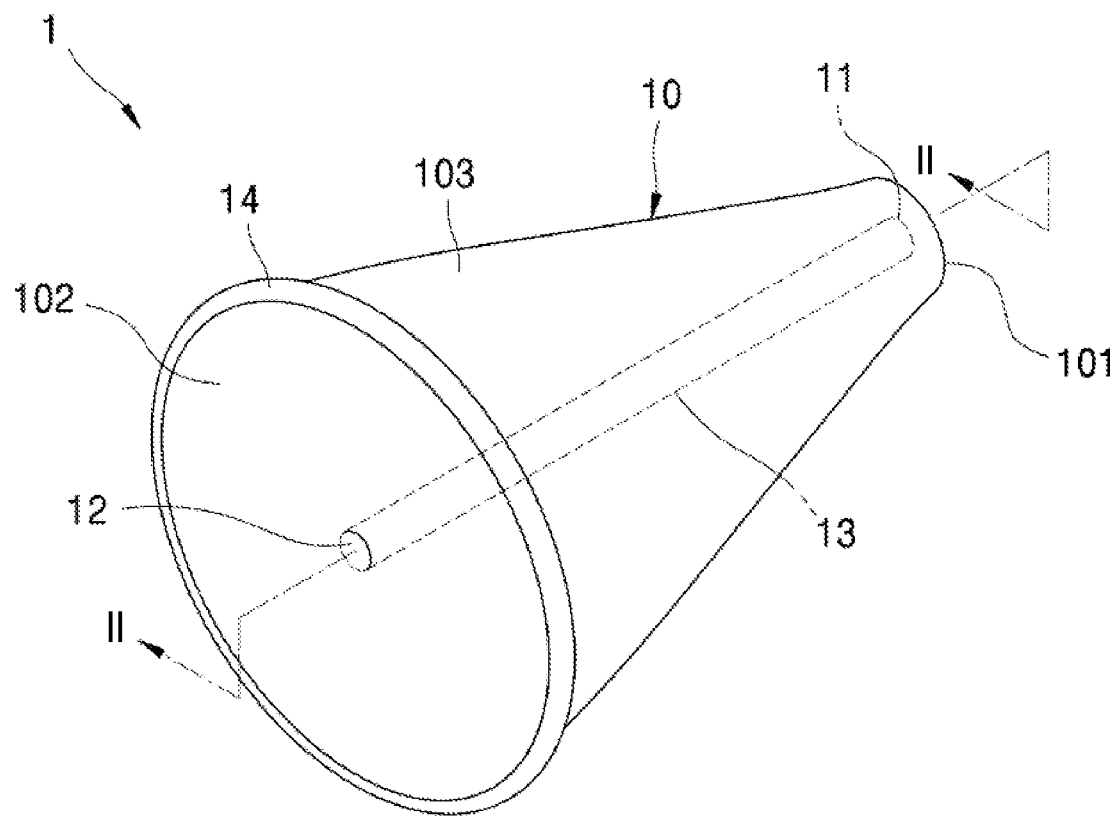
FIG. 1 is a perspective view of a first tip for intra-tympanic injection according to an embodiment.

As the disclosure allows for various changes and numerous embodiments, particular embodiments will be illustrated in the drawings and described in detail in the written description.

The effects and features of the disclosure and the accompanying methods thereof will become apparent from the following description of the embodiments, taken in conjunction with the accompanying drawings. However, the disclosure is not limited to the embodiments described below, and may be embodied in various modes.

Reference will now be made in detail to embodiments, examples of which are illustrated in the accompanying drawings. In the drawings, the same elements are denoted by the same reference numerals, and a repeated explanation thereof will not be given.

It will be understood that although the terms "first", "second", etc. may be used herein to describe various elements, these elements should not be limited by these terms. These elements are only used to distinguish one element from another.

As used herein, the singular forms "a," "an" and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

Sizes of elements in the drawings may be exaggerated for convenience of explanation. In other words, since sizes and thicknesses of components in the drawings are arbitrarily illustrated for convenience of explanation, the following embodiments are not limited thereto.

Figure 2:
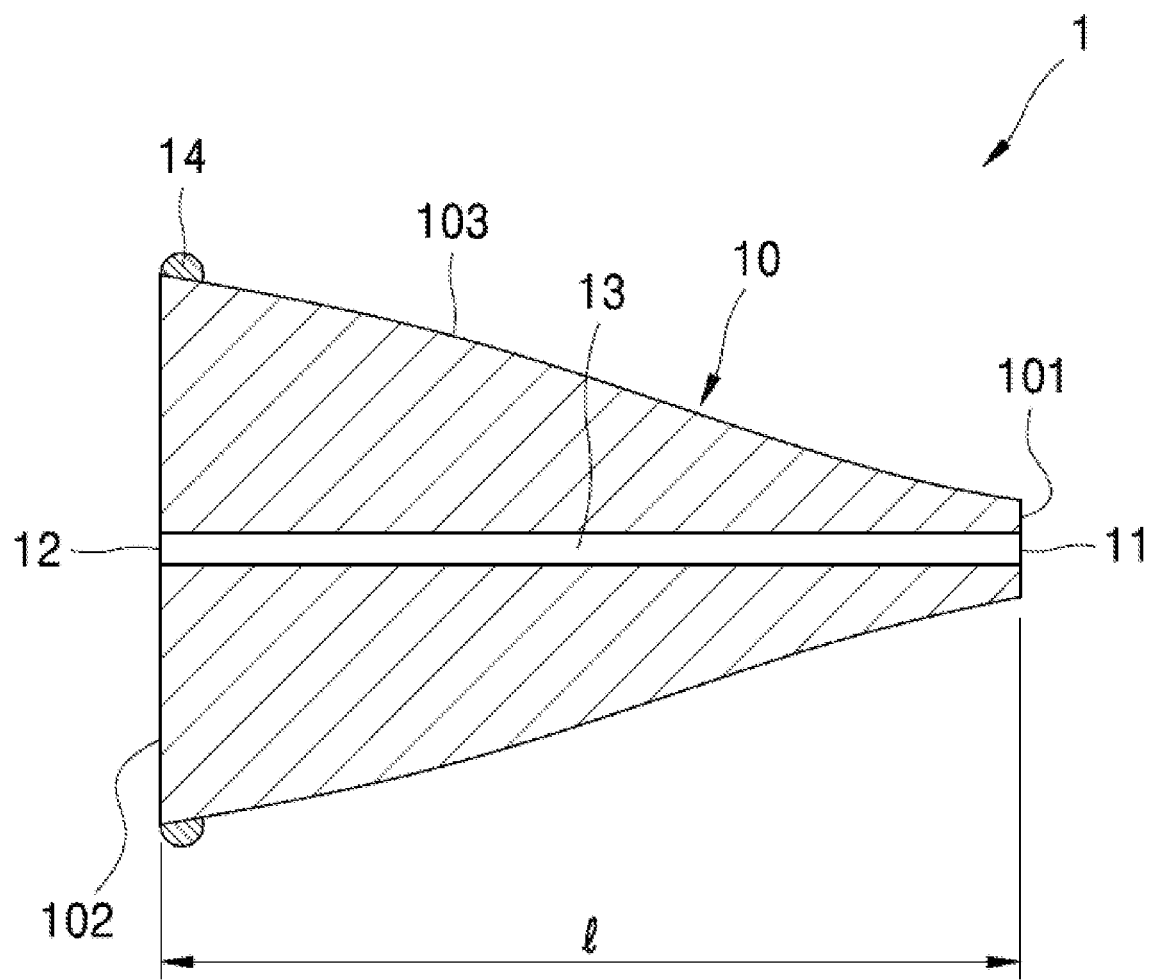
FIG. 2 is a cross-sectional view, taken along a line II-II of FIG. 1.

FIG. 1 is a perspective view of a first tip for intra-tympanic injection according to an embodiment, and FIG. 2 is a cross-sectional view taken along a line II-II of FIG. 1.

As shown in FIGS. 1 and 2, a first tip 1 for intra-tympanic injection according to an embodiment may include a first body 10 having an end portion 1-1 101 and an end portion 1-2 102, an opening 1-1 11 and an opening 1-2 12 formed in the first body 10, and a first communicating path 13 provided to penetrate through the first body 10.

The first body 10 is provided to be inserted into an external auditory meatus of a patient, wherein an outer surface 103 thereof may have a truncated cone-like shape to correspond to the shape of the external auditory meatus. The outer surface 103 may have a smooth surface, thereby minimizing irritation felt by a patient when inserted into an external auditory meatus.

Furthermore, the outer surface 103 may be provided in a linear shape in a direction from the end portion 1-1 101 toward the end portion 1-2 102, and, as described below, the end portion 1-1 101 may be formed smaller than the end portion 1-2 102 to facilitate insertion of the first tip 1 into an external auditory meatus of a patient. However, the disclosure is not necessarily limited thereto. At least the outer surface 103 may be formed to have predetermined elasticity, and thus the first body 10 may be well inserted into an external auditory meatus and maintain an unshakable state. This may be equally applied to all embodiments of the disclosure.

The first body 10 may include the end portion 1-1 101 and the end portion 1-2 102 facing each other. As described above, the end portion 1-1 101 may have a cross-section smaller than that of the end portion 1-2 102, such that the first body 10 is inserted into an external auditory meatus. When the first tip 1 for intra-tympanic injection is inserted into an external auditory meatus, the end portion 1-1 101 may be provided to have a cross-section smaller than the internal diameter of the external auditory meatus to be located close to an eardrum. Therefore, as described below, an injection needle may sufficiently come out through the opening 1-1 11 located at the end portion 1-1 101 to pierce an eardrum.

The length of the first body 10 may be defined as a distance 1 between the end portion 1-1 101 and the end portion 1-2 102, wherein the size of the cross-section of the end portion 1-1 101, the size of the cross-section of the end portion 1-2 102, and the distance 1 between the end portion 1-1 101 and the end portion 1-2 102 may be designed based on a distance between the end portion 1-1 101 and an eardrum when the first body 10 is inserted into an external auditory meatus. In other words, when the first body 10 is inserted into an external auditory meatus, the distance between the end portion 1-1 101 and an eardrum may be from about 1 mm to about 10 mm. According to an embodiment, the distance between the end portion 1-1 101 and the eardrum may be from about 1 mm to about 5 mm. The size of the cross-section of the end portion 1-1 101, the size of the cross-section of the end portion 1-2 102, and the length 1 between the end portion 1-1 101 and the end portion 1-2 102 may be set to maintain a short distance between the end portion 1-1 101 and an eardrum as described above.

The opening 1-1 11 may be located at the end portion 1-1 101, and the opening 1-2 12 may be located at the end portion 1-2 102. As shown in FIGS. 1 and 2, the opening 1-1 11 may be located at the center of the end portion 1-1 101, and the opening 1-2 12 may be located at the center of the end portion 1-2 102. However, the disclosure is not limited thereto, and the location(s) of the opening 1-1 11 and/or the opening 1-2 12 may be designed, such that an injection needle comes out from the opening 1-1 11 and is inserted into a correct location of an eardrum.

The opening 1-1 11 and the opening 1-2 12 may have the same size, wherein the opening 1-1 11 and opening 1-2 12 may be provided to have a diameter slightly greater than the diameter of an injection needle.

The sizes of the opening 1-1 11 and the opening 1-2 12 are not necessarily the same size, and the opening 1-1 11 and the opening 1-2 12 may have different sizes. In this case, the opening 1-1 11 may be provided smaller than the opening 1-2 12, wherein the opening 1-1 11 may have a diameter slightly greater than the diameter of an injection needle. When the opening 1-1 11 is provided smaller than the opening 1-2 12, it may be easier for a medical staff to insert an injection needle through the opening 1-2 12.

The first body 10 may be provided in a form in which the portion of the first body 10 inside the outer surface 103 is filled, wherein the outer surface 103 and the portion of the first body 10 inside the outer surface 103 the may be integrally formed.

The first communication path 13 connecting the opening 1-1 11 and the opening 1-2 12 may be further provided inside the first body 10.

The first communicating path 13 may be provided as a straight path, such that a needle of a syringe may pass therethrough. The size of the cross-section of the first communicating path 13 depends on the sizes of the opening 1-1 11 and the opening 1-2 12. When the opening 1-1 11 and the opening 1-2 12 are formed to have the same size, the first communicating path 13 may be formed to have the same cross-section size in a direction along the lengths of the first communicating path 13. When the openings 1-1 11 and the openings 1-2 12 are formed in different sizes, the size of the cross-section of the first communicating path 13 may be set to have a straight line gradient.

Although not shown, a separate hard material coating may be applied to the inner surface of the first communicating path 13 to prevent an injection needle from being stuck by piercing the inner surface of the first communicating path 13 when the injection needle passes through the first communicating path 13. The above-stated embodiment is applicable to all embodiments of the disclosure.

In some embodiments, according to an embodiment, a first handle 14 may be further provided outside the end portion 1-2 102 of the first body 10. The first handle 14 may be formed to form a closed loop along the outer edge of the end portion 1-2 102, wherein the first handle 14 may protrude outward, such that a user may easily hold the first tip 1 for intra-tympanic injection in case of inserting or removing the first tip 1 for intra-tympanic injection to or from an external auditory meatus of a patient. However, the disclosure is not limited thereto. Unlike as shown in the drawing, the first handle 14 may have any shape as long as the first handle 14 is inserted to the first body 10 and has a shape sufficient for a user to remove the first body 10 inserted to an ear. Also, the first handle 14 is not limited to being formed to form a single closed loop as shown in the drawing and may be formed as a plurality of protrusions arranged discontinuously. Therefore, the first handle 14 may separate from the inner surface of a second tip when the first tip 1 for intra-tympanic injection is coupled to the second tip in another embodiment described below. The first handle 14 may be formed optionally and is not necessarily applicable to all embodiments of the disclosure.

The first tip 1 for intra-tympanic injection as described above may be used in a surgery and/or a therapy in which an injection needle is inserted through an eardrum.

Figure 3:
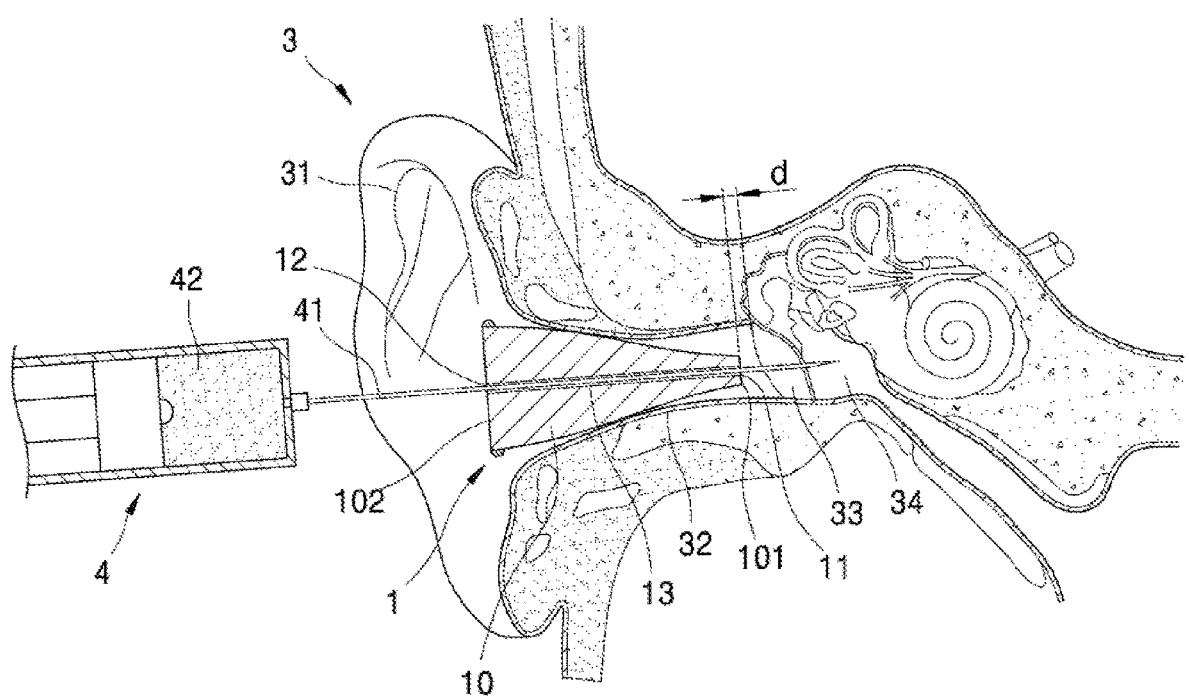
FIG. 3 is a schematic cross-sectional view of a state of an intra-tympanic injection by using a first tip for intra-tympanic injection according to an embodiment.

Referring to FIG. 3, in an ear 3 of a human body, an external auditory meatus 32 extends to an eardrum 33 inside an auricle 31, and a tympanum 34 is located beyond the eardrum 33. In other words, the eardrum 33 is located between the external auditory meatus 32 and the tympanum 34.

A practitioner may insert the first tip 1 for intra-tympanic injection to the external auditory meatus 32. With the first tip 1 for intra-tympanic injection is sufficiently inserted into the external auditory meatus 32, a distance d between a first end portion 101 and the eardrum 33 may be from about 1 mm to about 10 mm. According to an embodiment, the distance d between the first end portion 101 and the eardrum 33 may be may be from about 1 mm to about 5 mm. When the first tip 1 for intra-tympanic injection is sufficiently inserted to the external auditory meatus 32, the opening 1-1 11 located at the end portion 1-1 101 is located at an injecting location of the eardrum 33.

A practitioner may insert an injection needle 41 located at the sharp end of a syringe 4 into the first communicating path 13 through a second opening of the end portion 1-2 102, such that the injection needle 41 pierces the eardrum 33 through the first communicating path 13. The practitioner may further insert the injection needle 41 to the tympanum 34 beyond the eardrum 33, thereby injecting a drug 42 to the tympanum 34.

When the practitioner pierces the eardrum 33 with the injection needle 41, the practitioner may use the first tip 1 for intra-tympanic injection according to one embodiment, thereby preventing the practitioner from piercing regions other than the eardrum 33 with the injection needle 41. Also, even when the practitioner is unable to visually determine the location of the eardrum 33 due to blood or other foreign objects inside the external auditory meatus 32, since the opening 1-1 11 is located close to the eardrum 33, the injection needle 41 passed through the first communicating path 13 may accurately pierce the eardrum 33, thereby improving accuracy of a surgery and reducing discomfort and pain of a patient.

Figure 4:
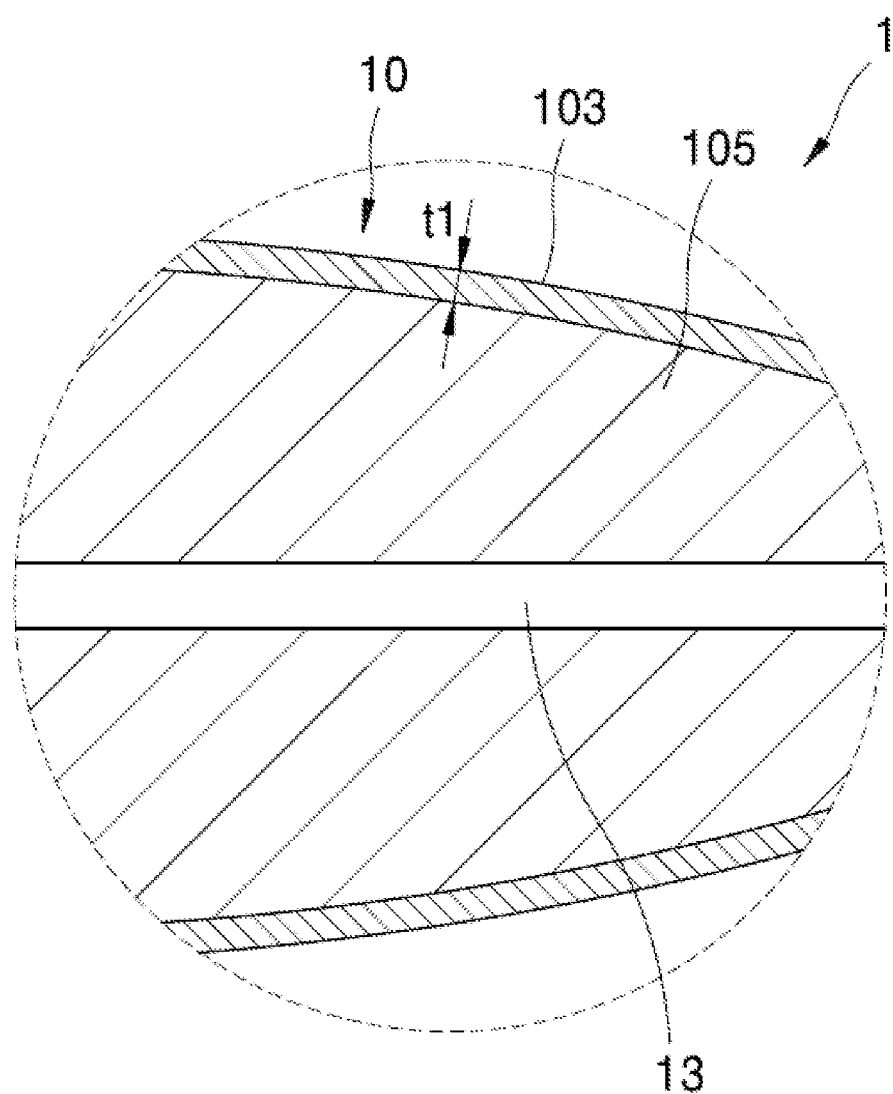
FIG. 4 is a cross-sectional view of a portion of a first tip for intra-tympanic injection according to another embodiment.

FIG. 4 is a cross-sectional view of a portion of the first tip 1 for intra-tympanic injection according to another embodiment.

According to the embodiment shown in FIG. 4, the first body 10 may include a first outer casing 104 and a filling portion 105.

The first outer casing 104 may include the outer surface 103 outside and may be arranged, such that the outer surface 103 is in close contact with an external auditory meatus.

The filling portion 105 may be located inside the first outer casing 104, and the first communicating path 13 may be formed in the filling portion 105.

According to an embodiment, the first outer casing 104 may include a hard plastic material or a metal. In some embodiments, the first outer casing 104 may be in a form same as and/or similar to an auriscope tip. This first outer casing 104 may have a first thickness t1, wherein the first thickness t1 may be as small as possible. The filling portion 105 filling the interior of the first outer casing 104 may include a plastic material, wherein the filling portion 105 may include a hard plastic material to prevent an injection needle from piercing the first communicating path 13.

In some embodiments, according to another embodiment, the first outer casing 104 may be provided to have elasticity. To this end, the first outer casing 104 may include a flexible material, such as silicon and/or polyurethane. In this case, the first thickness t1 of the first outer casing 104 may be greater than that in the case where the first outer casing 104 includes a plastic material or a metal as in the above-described embodiment. However, even in this case, the filling portion 105 may include a hard plastic material to prevent an injection needle from piercing the first communicating path 13.

In a case where the first outer casing 104 includes a flexible material, when the first body 10 is inserted to an external auditory meatus, the outer surface 103 of the first body 10 may flexibly deformed to some extent according to the shape of the external auditory meatus, thereby facilitating insertion of the first body 10 to the external auditory meatus to an appropriate depth.

This may be equally applied to all embodiments of the disclosure.

Figure 5:
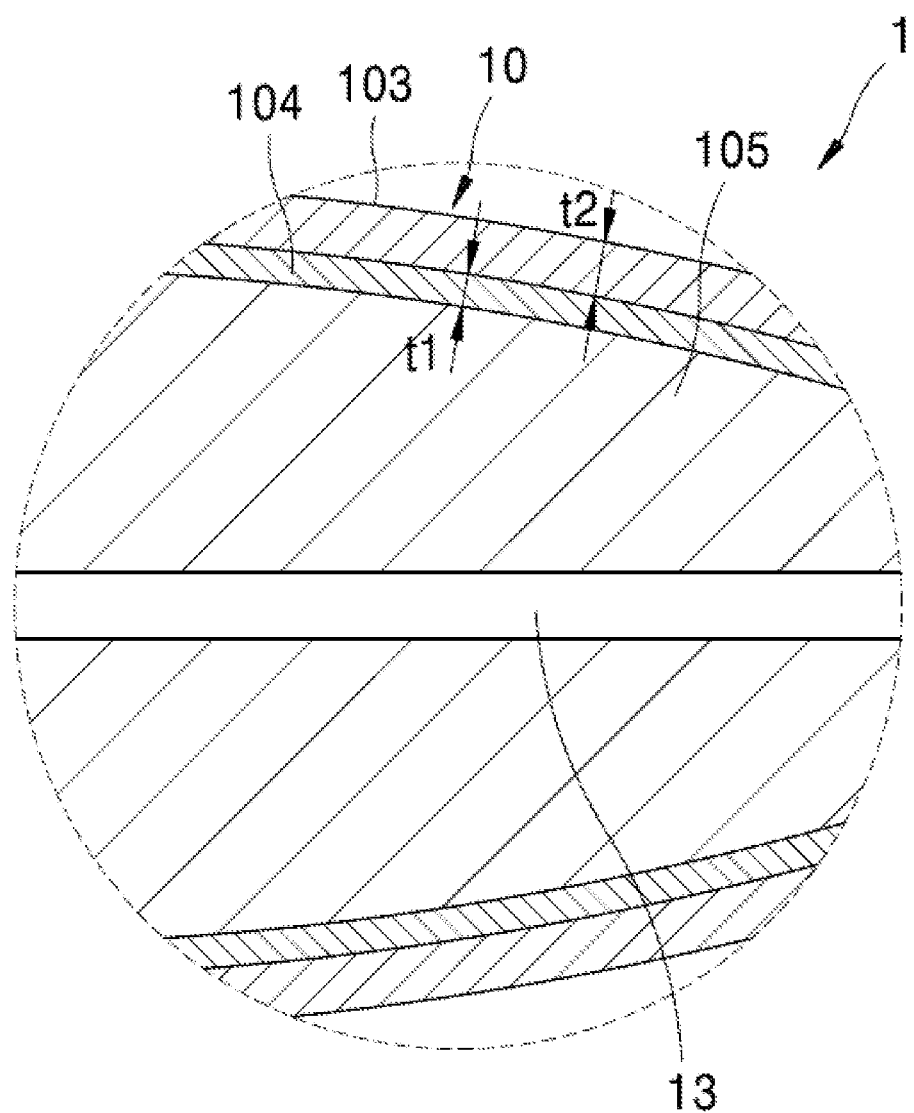
FIG. 5 is a cross-sectional view of a portion of a first tip for intra-tympanic injection according to another embodiment.

FIG. 5 is a cross-sectional view of a portion of the first tip 1 for intra-tympanic injection according to another embodiment.

According to the embodiment shown in FIG. 5, the first body 10 may include the first outer casing 104, a second outer casing 106, and the filling portion 105.

The second outer casing 106 may include the outer surface 103 outside and may be arranged, such that the outer surface 103 is in close contact with an external auditory meatus.

The first outer casing 104 may be located to contact the inner surface of the second outer casing 106, and the filling portion 105 may be located inside the first outer casing 104. The first communicating path 13 may be formed in the filling portion 105.

According to an embodiment, the first outer casing 104 may include a hard plastic material or a metal. In some embodiments, the first outer casing 104 may be in a form same as and/or similar to an auriscope tip. The filling portion 105 filling the interior of the first outer casing 104 may include a plastic material, wherein the filling portion 105 may include a hard plastic material to prevent an injection needle from piercing the first communicating path 13. The second outer casing 106 located outside the first outer casing 104 may include a flexible material, such as silicon and/or polyurethane.

In a case where the first outer casing 104 includes a hard material and the second outer casing 106 includes a flexible material, when the first body 10 is inserted to an external auditory meatus, the outer surface 103 of the first body 10 may flexibly deformed to some extent according to the shape of the external auditory meatus, thereby facilitating insertion of the first body 10 to the external auditory meatus to an appropriate depth. Meanwhile, the first outer casing 104 may maintain the shape of the first body 10 constantly without being deformed.

The first thickness t1 of the first outer casing 104 may be smaller than a second thickness t2 of the second outer casing 106, thereby preventing a patient from feeling discomfort when the outer surface 103 of the first body 10 contacts an external auditory meatus.

This may be equally applied to all embodiments of the disclosure.

Figure 6:
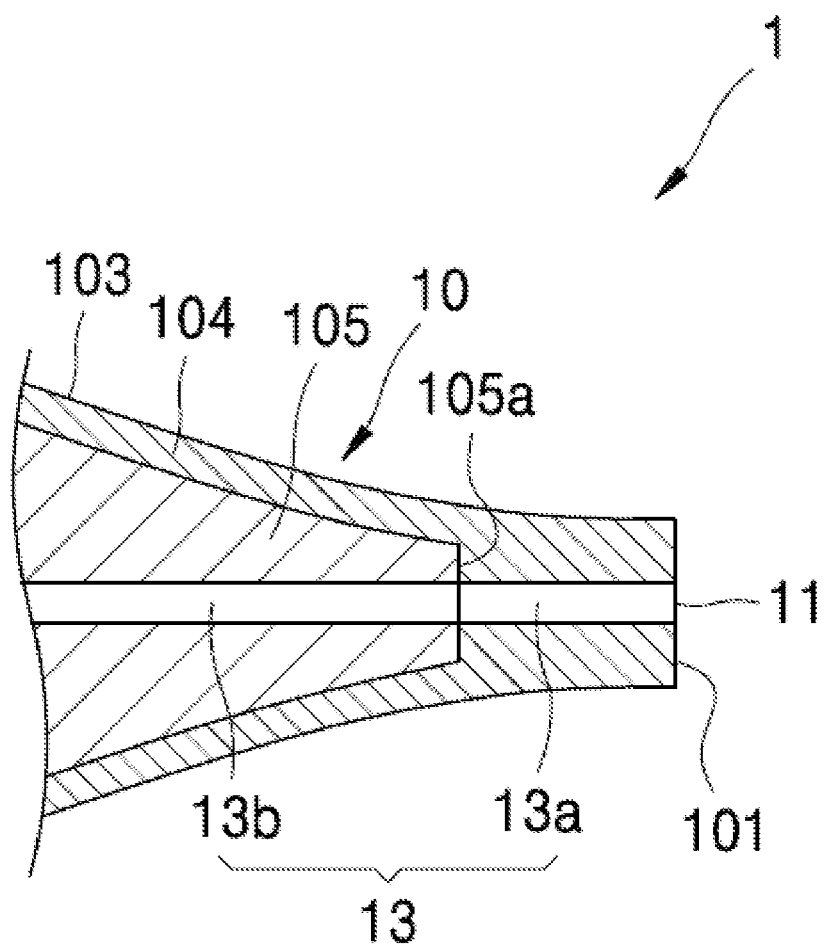
FIG. 6 is a cross-sectional view of a portion of a first tip for intra-tympanic injection according to another embodiment.

FIG. 6 is a cross-sectional view of a portion of the first tip 1 for intra-tympanic injection according to another embodiment.

According to the embodiment shown in FIG. 6, the first outer casing 104 is provided to be in close contact with the outer surface of the filling portion 105, wherein the first outer casing 104 may extend to cover a sharp end 105a of the filling portion 105. Therefore, the sharp end of the first outer casing 104 may become the end portion 1-1 101. In this case, the first outer casing 104 may include a flexible material as described above. Therefore, the end portion 1-1 101 may also include a flexible material.

The first communicating path 13 may include a first communicating path 13a formed in the first outer casing 104 and a second communicating path 13b formed in the filling portion 105, and the first communicating path 13a and second communicating path 13b may be linearly connected to each other.

According to the present embodiment, when the first body 10 is inserted to an external auditory meatus of a patient, since the end portion 1-1 101 includes a flexible material, a patient may not feel sharp pain even when the end portion 1-1 101 contacts an eardrum of the patient, and thus discomfort of the patient may be reduced.

This may be equally applied to all embodiments of the disclosure. For example, although not shown, when the embodiment shown in FIG. 6 is applied to the embodiment shown in FIG. 5, the end portion 1-1 101 may be formed by the second outer casing 106.

Figure 7:
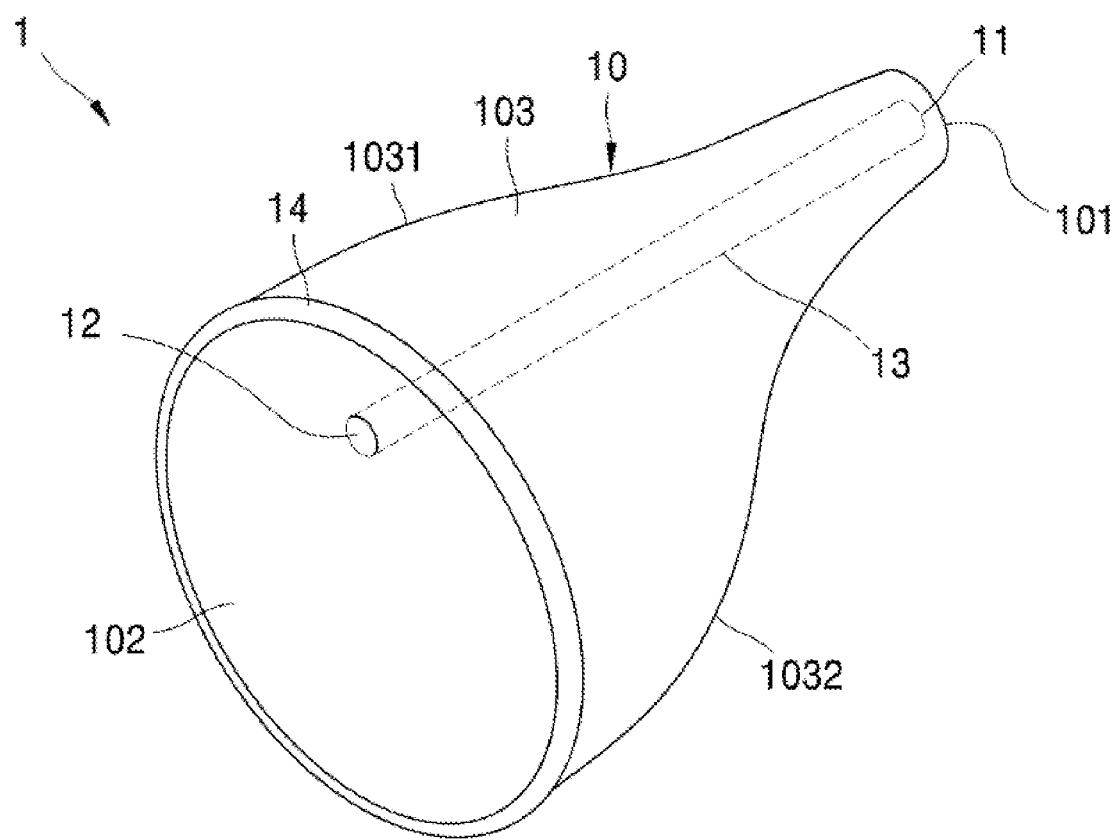
FIG. 7 is a perspective view of a portion of a first tip for intra-tympanic injection according to another embodiment.

FIG. 7 is a perspective view of a portion of the first tip 1 for intra-tympanic injection according to another embodiment.

According to the embodiment shown in FIG. 7, the outer surface 103 of the first body 10 may have a curved shape. The outer surface 103 may be curved in a shape corresponding to the shape of an external auditory meatus. Therefore, it may be easier to insert the first body 10 into an external auditory meatus.

In detail, the outer surface 103 may include a first outer surface 1031 facing upward and a second outer surface 1032 facing downward. The first outer surface 1031 may form a large wave pattern, and the second outer surface 1032 below the first body 10 may have a greater curvature than the first outer surface 1031 located above. Therefore, the first body 10 may be formed to correspond to the shape of an external auditory meatus to maintain a close contact with the external auditory meatus. Furthermore, since the shape of the outer surface 103 of the first body 10 corresponds to the shape of the external auditory meatus, the opening 1-1 11 may be located to face an accurate injection location of an eardrum without any adjustment by simply inserting the first body 10 to the external auditory meatus.

In some embodiments, it is not necessary for the opening 1-2 12 to be located at the center of the end portion 1-2 102 and may be located eccentrically from the center of the end portion 1-2 102 as shown in FIG. 7. The opening 1-1 11 may also be located eccentrically from the center of the end portion 1-1 101. However, when the size of the end portion 1-1 101 is small, the opening 1-1 11 may be located at the center of the end portion 1-1 101. Even in this embodiment, the first communicating path 13 may be formed linearly to connect the openings 1-1 11 and the openings 1-2 12. When the opening 1-2 12 is located eccentrically from the center of the end portion 1-2 102, and more particularly, when the opening 1-2 12 is located above the end portion 1-2 102, it may be more convenient for a practitioner to insert an injection needle to the first communicating path 13 through the opening 1-2 12.

This may be equally applied to all embodiments of the disclosure.

Figure 8:
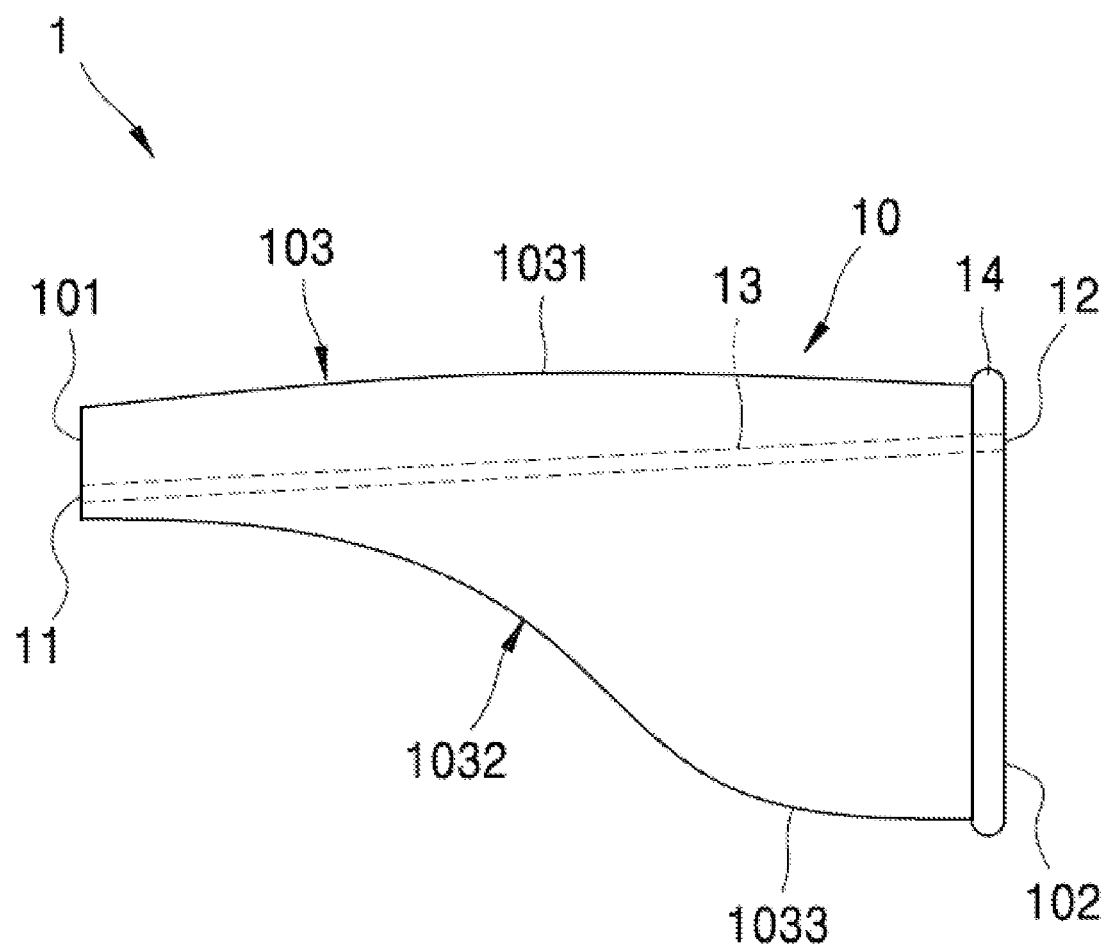
FIG. 8 is a perspective view of a portion of a first tip for intra-tympanic injection according to another embodiment.
Figure 9:
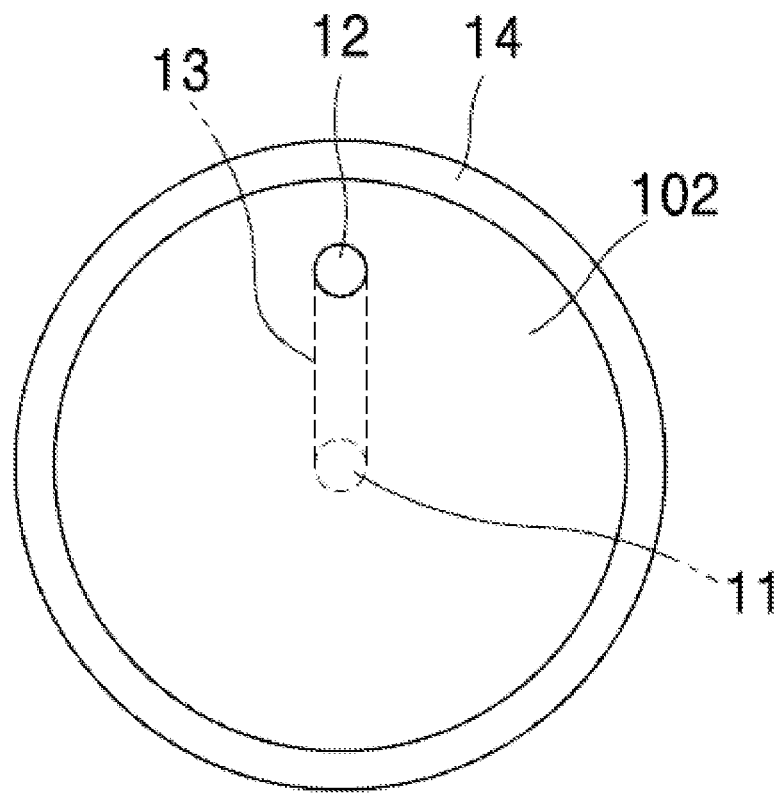
FIG. 9 is a perspective view of a portion of a first tip for intra-tympanic injection according to another embodiment.

FIGS. 8 and 9 are a side view and a rear view of the first tip 1 for intra-tympanic injection according to another embodiment.

According to the embodiments shown in FIGS. 8 and 9, the outer surface 103 of the first body 10 may have a curved shape. The outer surface 103 may be curved in a shape corresponding to the shape of an external auditory meatus. Therefore, it may be easier to insert the first body 10 into an external auditory meatus.

In detail, the outer surface 103 may include a first outer surface 1031 facing upward and a second outer surface 1032 facing downward. The first outer surface 1031 may be formed in a substantially linear shape or an arc having a large radius of curvature, and the second outer surface 1032 located below the first body 10 may be formed to be bent in an S shape. Particularly, a portion 1033 closer to the end portion 1-2 102 from the center may protrude more significantly. Such a shape of the outer surface 103 becomes more similar to the shape of the external auditory meatus, and thus the opening 1-1 11 may be located to face an accurate injection location of an eardrum without any adjustment by simply inserting the first body 10 to the external auditory meatus.

In some embodiments, the opening 1-1 11 and the opening 1-2 12 may be located symmetrically with each other and eccentrically from the respective centers of the end portion 1-1 101 and the end portion 1-2 102. For example, the opening 1-2 12 may be located eccentrically upward from the center of the end portion 1-2 102, whereas the opening 1-1 11 may be eccentrically downward from the center of the end portion 1-1 101. The first communicating path 13 may be formed linearly to connect the openings 1-1 11 and the openings 1-2 12.

The locations of the opening 1-1 11 and the opening 1-2 12 not only facilitate insertion of an injection needle by a practitioner into the first communicating path 13 through the opening 1-2 12, but also enables insertion of the injection needle to a correct location simply by inserting the injection needle.

This may be equally applied to all embodiments of the disclosure.

Figure 10:
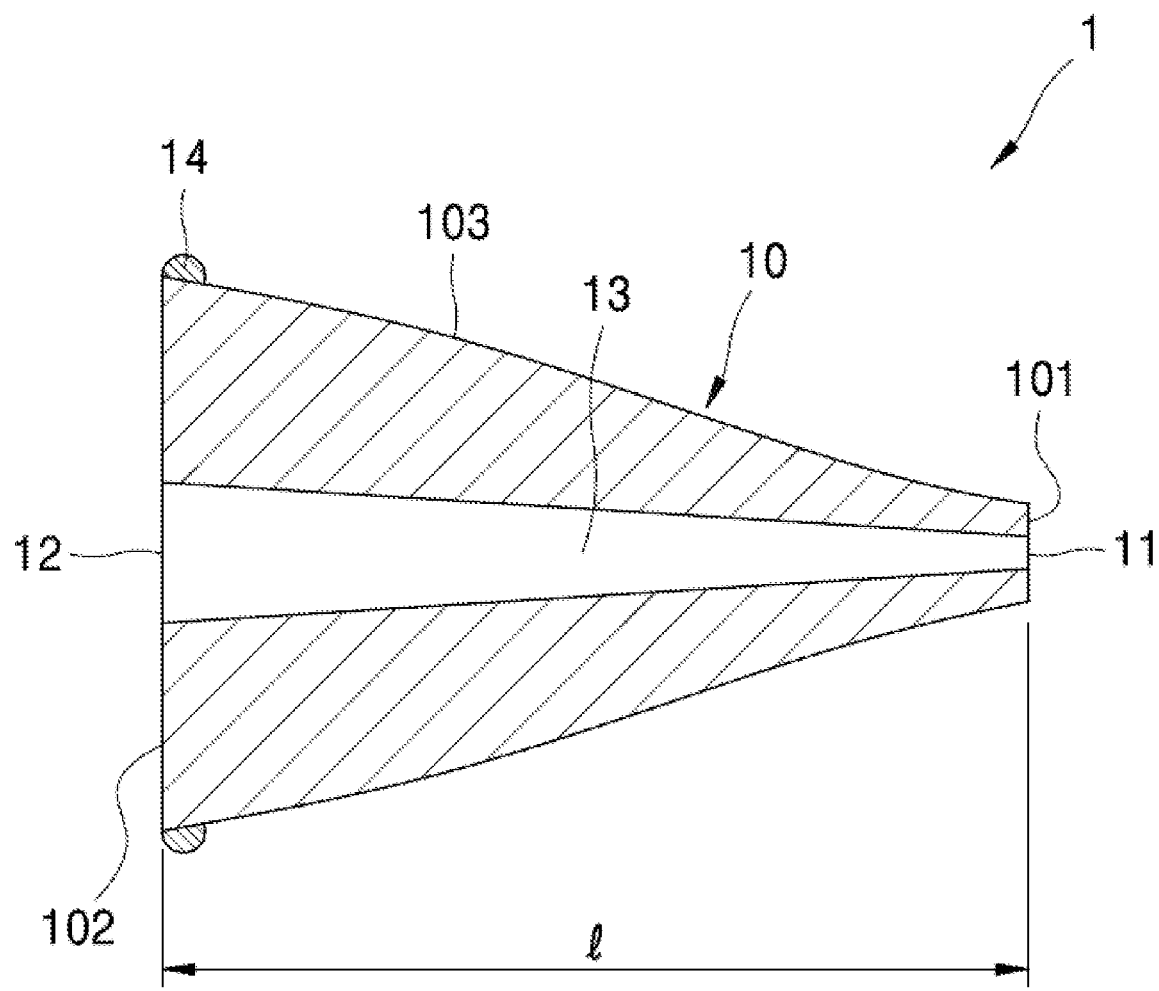
FIG. 10 is a perspective view of a portion of a first tip for intra-tympanic injection according to another embodiment.

FIG. 10 is a cross-sectional view of the first tip 1 for intra-tympanic injection according to another embodiment.

According to the embodiment shown in FIG. 10, the first communicating path 13 may be provided to have different diameters in the lengthwise direction of the first body 10. In other words, the diameter of the opening 1-1 11 and the diameter of the opening 1-2 12 extending from the first communicating path 13 may be different from each other.

According to an embodiment, the diameter of the opening 1-1 11 may be smaller than the diameter of the opening 1-2 12. Therefore, a user may easily insert an injection needle from the opening 1-2 12. Also, the opening 1-1 11 may aim a target more accurately, and thus an injection needle passing through the opening 1-1 11 may be prevented from piercing an external auditory meatus instead of an eardrum.

The first communicating path 13 may extend linearly from the opening 1-1 11 to the opening 1-2 12, and thus the first communicating path 13 may have a shape that the diameter thereof gradually increases at a constant rate from the opening 1-1 11 to the opening 1-2 12.

Figure 11:
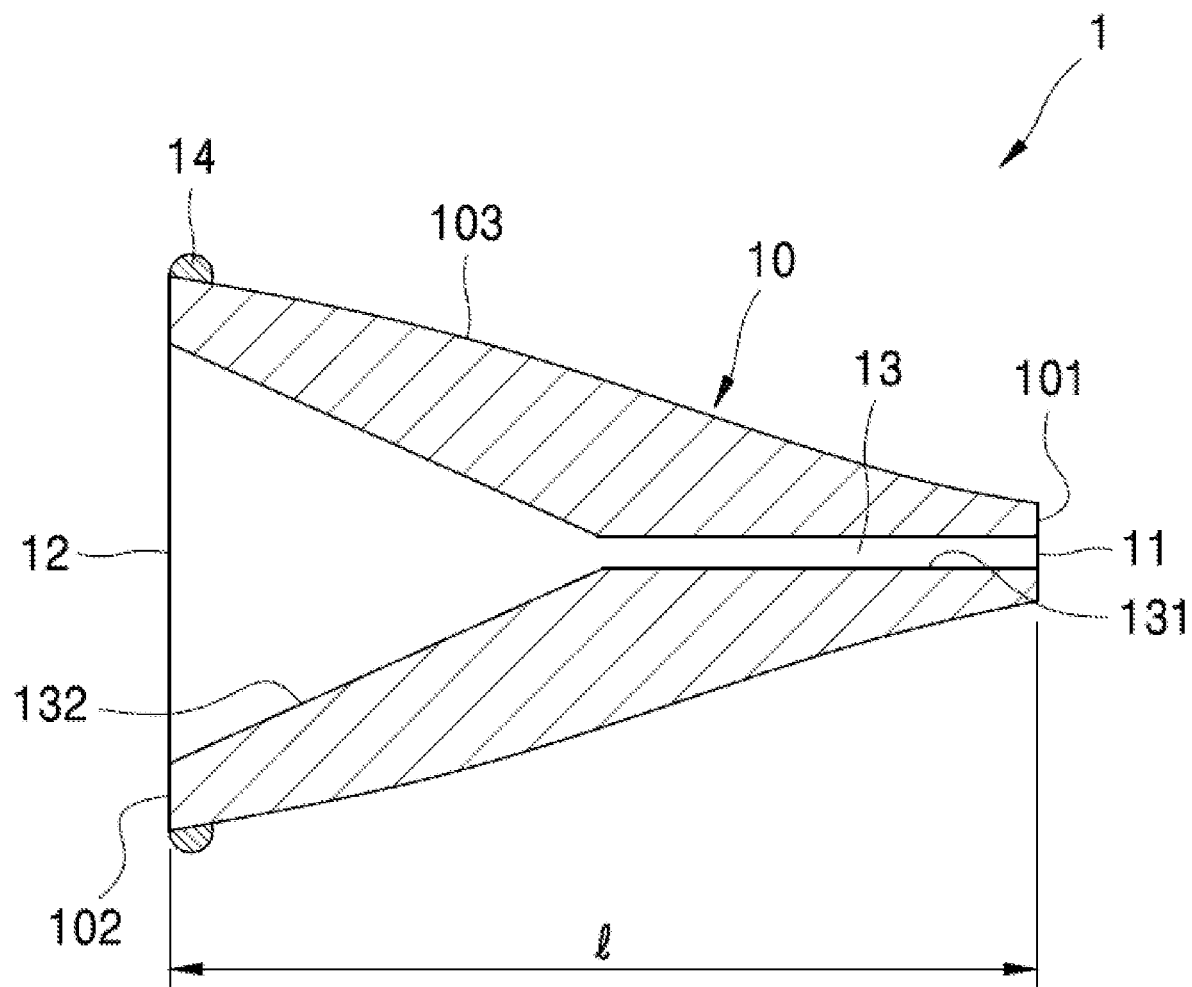
FIG. 11 is a perspective view of a portion of a first tip for intra-tympanic injection according to another embodiment.

However, the disclosure is not necessarily limited thereto, and as shown in FIG. 11, the first communicating path 13 may include a communicating path 1-1 131 and a communicating path 1-2 132 having different diameters. FIG. 11 is a cross-sectional view of the first tip 1 for intra-tympanic injection according to another embodiment.

The communicating paths 1-1 131 may extend from the opening 1-1 11 with the same diameter or a slightly increased diameter toward the opening 1-2 12. Thereafter, the communicating path 1-1 131 is connected to the communicating path 1-2 132, wherein the communicating path 1-2 132 may extend in a shape that the diameter thereof increases toward the opening 1-2 12. The rate at which the diameter of the communicating path 1-2 132 increases may be greater than the rate at which the diameter of the communication path 1-1 131 increases. Therefore, the communicating paths 1-2 132 may form a steeper slope than the communicating path 1-1 131.

In the first tip 1 for intra-tympanic injection having the structure as described above, since the opening 1-2 12 is larger than in the embodiment shown in FIG. 10, a user may easily observe inside an ear through the opening 1-2 12, and thus the opening 1-1 11 may aim an eardrum more accurately.

Also, since the diameter of the communication path 1-1 131 is constant or slightly increases for a certain length, the structure may facilitate straight movement of an injection needle passing through the communication path 1-1 131, and thus the injection needle may pierce an eardrum more accurately. As such, the communicating path 1-1 131 may include at least a straight portion that guides an injection needle, wherein the straight portion may extend slightly from the opening 1-1 11 in the direction toward the opening 1-2 12. For example, the straight portion may be formed to extend about 1 mm or more from the opening 1-1 11. The extension length may be appropriately selected to guide an injection needle. This may be equally applied to all embodiments of the disclosure.

Figure 12:
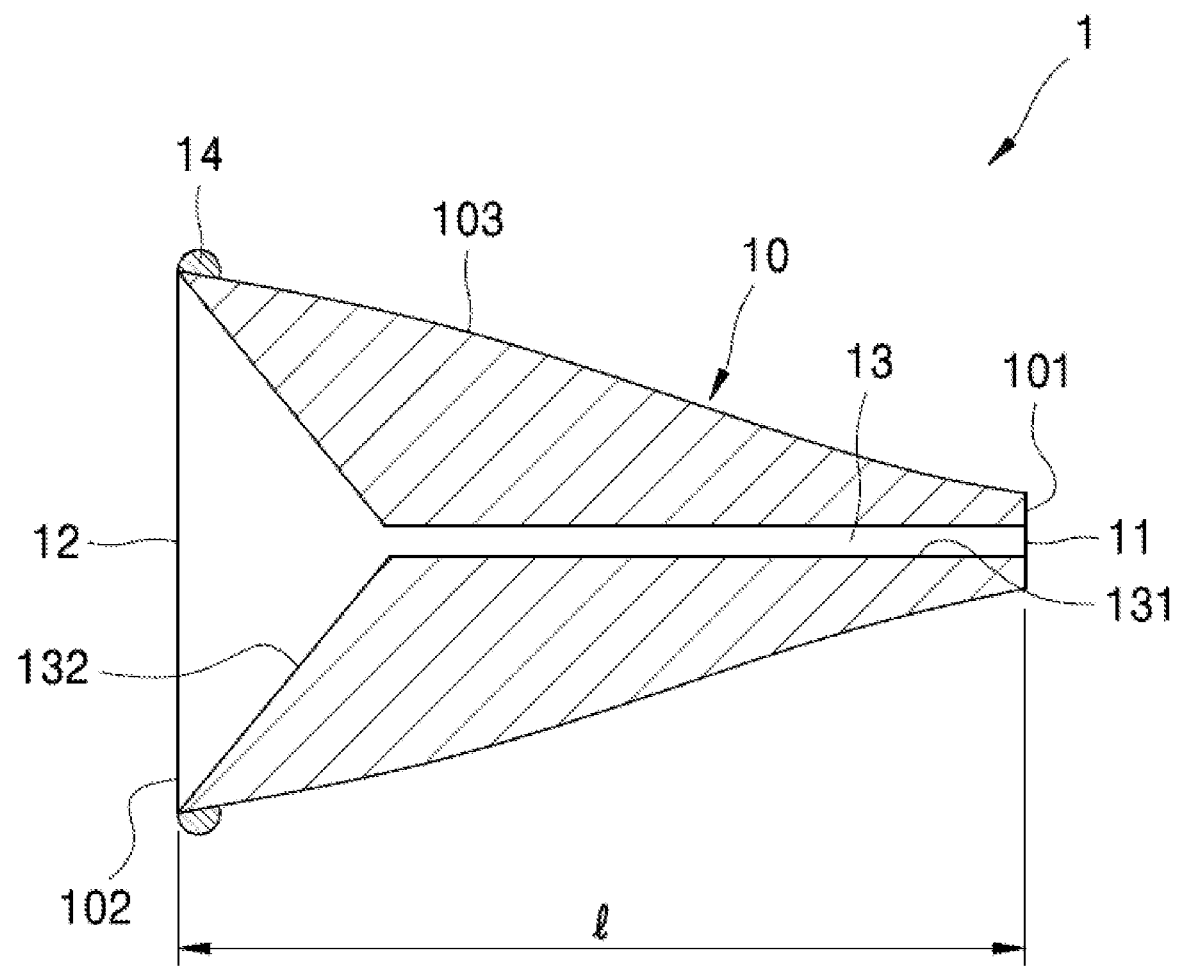
FIG. 12 is a perspective view of a portion of a first tip for intra-tympanic injection according to another embodiment.

On the other hand, in a structure as described above, the diameter of the opening 1-2 12 may be smaller than the diameter of the end portion 1-2 102. However, the disclosure is not necessarily limited thereto. As in the first tip 1 for intra-tympanic injection according to another embodiment shown in FIG. 12, the diameter of opening 1-2 12 may be equal to the diameter of end portion 1-2 102. Therefore, in this case, the opening 1-2 12 may be formed along the edge of the end portion 1-2 102.

In the first tip 1 for intra-tympanic injection according to the embodiments of the disclosure described above, the first communicating path 13 may be at least partially provided in a linear shape, thereby guiding the entry of an injection needle.

Figure 13:
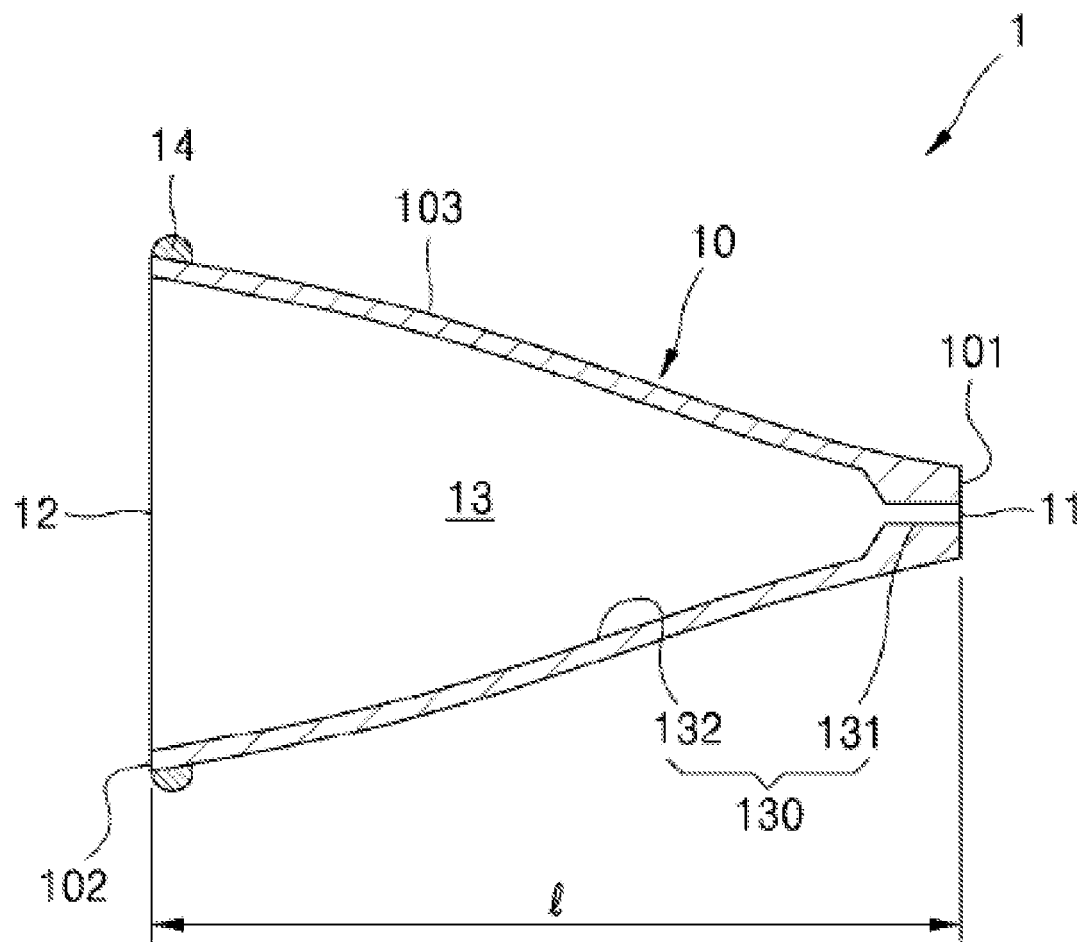
FIG. 13 is a perspective view of a portion of a first tip for intra-tympanic injection according to another embodiment.

FIG. 13 is a cross-sectional view of the first tip 1 for intra-tympanic injection according to another embodiment.

Unlike in the above-described embodiment, in the embodiment shown in FIG. 13, the communication path 1-2 132 may be provided more widely and extend with a constant thickness along the outer surface 103 of the first body 10. The communication path 1-1 131 may be formed in a linear shape, wherein the length of the communicating path 1-1 131 may be about 1 mm or greater, e.g., from about 2 mm to about 3 mm. In the first tip 1 for intra-tympanic injection having such a structure, the length of the communication path 1-1 131 may be small, thereby facilitating a surgery by a practitioner.

Figure 14:
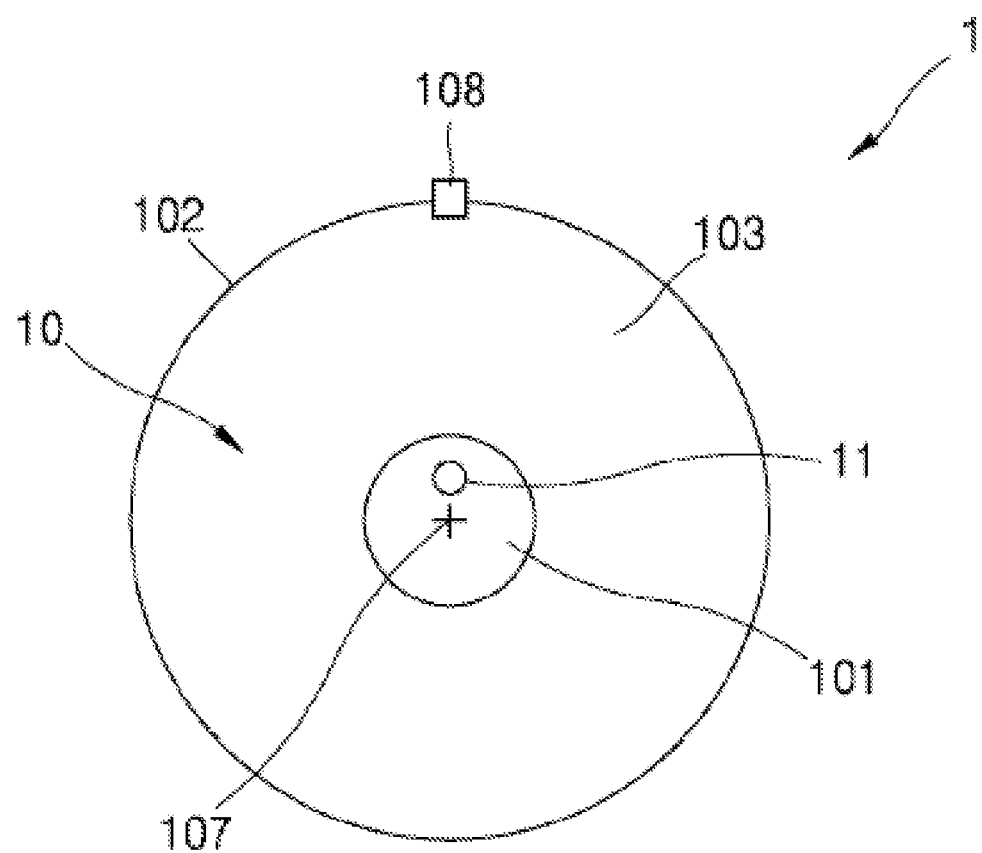
FIG. 14 is a perspective view of a portion of a first tip for intra-tympanic injection according to another embodiment.

As shown in FIG. 14, the opening 1-1 11 may be located at a location eccentric to one side from a center 107 of the end portion 1-1 101. At this time, at least one guide 108 may be installed on the outer surface 103 and/or the inner surface of the first body 10 to allow a practitioner to recognize the location of the opening 1-1 11. It is not necessary to form the guide 108 on the outer surface 103, and the guide 108 may be formed on the inner surface. Also, it is not necessary to form the guide 108 in a direction close to the opening 1-1 11, and the guide 108 may be formed in a direction opposite thereto. In other words, the guide 108 may be formed at any location as long as a practitioner may recognize the location of the opening 1-1 11 with the guide 108.

The first tip 1 for intra-tympanic injection of the embodiments shown in FIGS. 10 to 14 may be applied to all embodiments of the disclosure.

On the other hand, the first tip 1 for intra-tympanic injection according to the above-stated embodiments may be inserted to an external auditory meatus of a patient to allow an injection needle to penetrate through an eardrum. However, the disclosure is not necessarily limited thereto, and the first tip 1 for intra-tympanic injection may be used in combination with a separate second tip 2 as shown in FIGS. 15 and 16.

Figure 15:
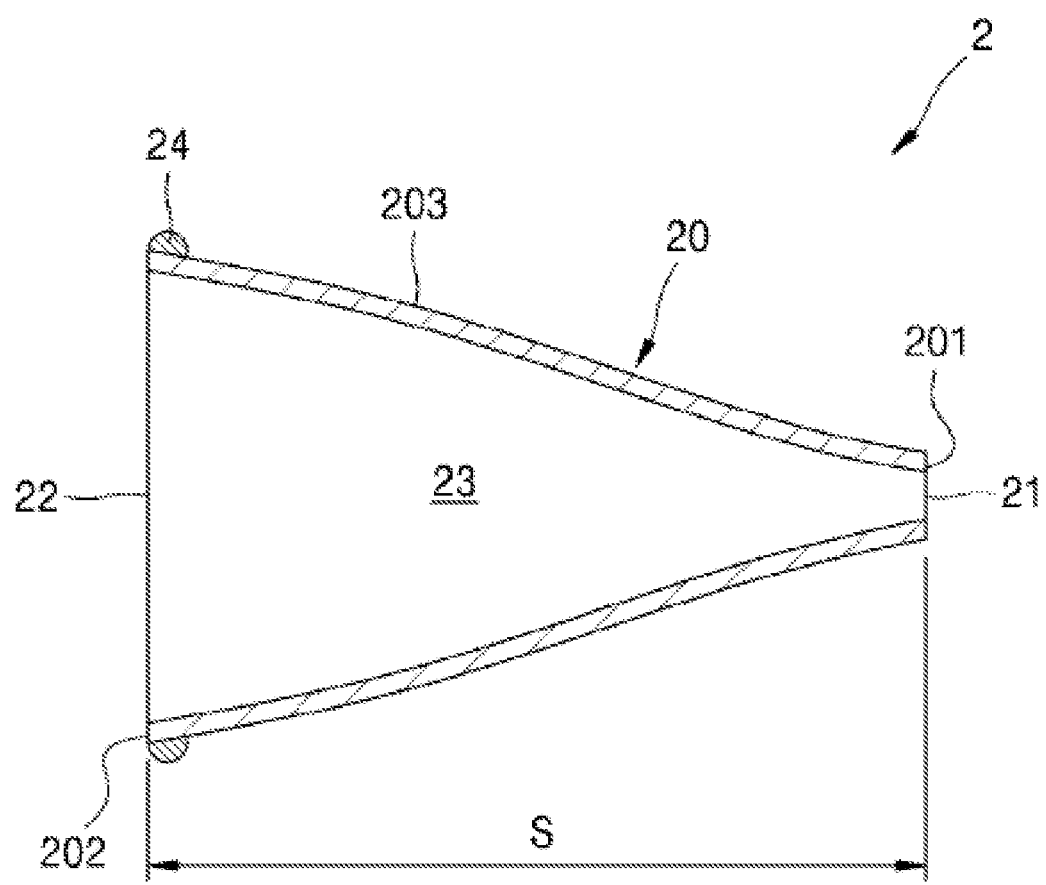
FIG. 15 is a cross-sectional view of a second tip according to an embodiment.
Figure 16:
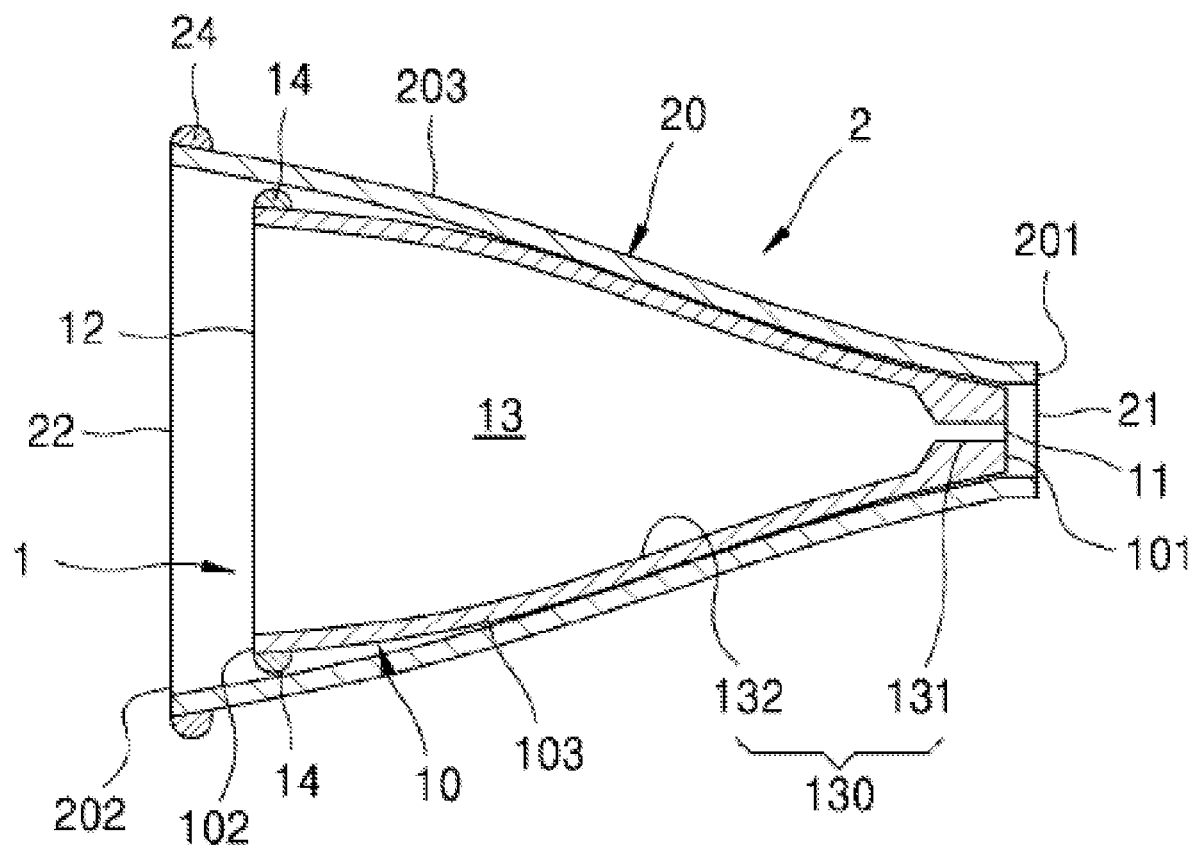
FIG. 16 is a cross-sectional view showing another embodiment in which a first tip for intra-tympanic injection and a second tip are coupled to each other.

FIG. 15 is a cross-sectional view of a second tip 2 according to an embodiment of the disclosure.

Referring to FIG. 15, the second tip 2 may include a second body 20 having an end portion 2-1 201 and an end portion 2-2 202, an opening 2-1 21 and an opening 2-2 22 located in the second body 20, and a second communication path 23 provided to penetrate through the second body 20.

The second body 20 is provided to be inserted into an external auditory meatus of a patient, wherein an outer surface 203 thereof may have a truncated cone-like shape to correspond to the shape of the external auditory meatus. The outer surface 203 may have a smooth surface, thereby minimizing irritation felt by a patient when inserted into an external auditory meatus.

Furthermore, the outer surface 203 may be provided in a linear shape in a direction from the end portion 2-1 101 toward the end portion 2-2 102 and may be formed to have one or more curvatures to facilitate insertion of the second tip 2 into an external auditory meatus of a patient. At least the outer surface 203 may include a metal and/or a plastic material, but is not limited thereto. At least the outer surface 203 may be formed to have a predetermined elasticity, such that the second body 20 may be inserted into an external auditory meatus unshakably.

The second body 20 may include the end portion 2-1 201 and the end portion 2-2 202 facing each other. As described above, the end portion 2-1 201 may have a cross-section smaller than that of the end portion 2-2 202, such that the second body 20 is inserted into an external auditory meatus. When the second tip 2 is inserted into an external auditory meatus, the end portion 2-1 201 may be provided to have a cross-section smaller than the internal diameter of the external auditory meatus to be located close to an eardrum.

In some embodiments, according to an embodiment, a second handle 24 may be further provided outside the end portion 2-2 202 of the second body 20. The second handle 24 may be formed along the outer edge of the end portion 2-2 202, wherein the second handle 24 may protrude outward, such that a user may easily hold the second tip 2 in case of inserting or removing the second tip 2 to or from an external auditory meatus of a patient. However, the disclosure is not limited thereto. Unlike as shown in the drawing, the second handle 24 may have any shape as long as the second handle 24 is inserted to the second body 20 and has a shape sufficient for a user to remove the second body 20 inserted to an ear.

The length S of the second body 20 may be defined as a distance between the end portion 2-1 201 and the end portion 2-2 202 and may be set as a length sufficient to expose the end portion 2-2 202 out of an ear when the second body 20 is inserted to an external auditory meatus. The second body 20 may be formed in the same thickness from the end portion 2-1 201 to the end portion 2-2 202. However, the disclosure is not necessarily limited thereto, and the second body 20 may be formed to provide appropriate thickness variation for the first tip 1 to be coupled to the inner surface 204. The opening 2-1 21 may be located at the end portion 2-1 201, and the opening 2-2 22 may be located at the end portion 2-2 202. As shown in FIG. 15, the opening 2-1 21 may be smaller than the opening 2-2 22. The second communicating path 23 is located between the opening 2-1 21 and the opening 2-2 22, and the second communicating path 23 may be defined by the shape of the inner surface 204 of the second body 20. The inner surface 204 may be formed to have a smooth surface to facilitate attachment and detachment of the first tip 1 of the above-described embodiments.

As shown in FIG. 16, the first tip 1 of the above-described embodiments may be inserted to the second communication path 23 of the second tip 2, such that an injection needle penetrate through the first tip 1. In other words, a medical staff may first insert the second tip 2 into an ear of a patient to more clearly observe the condition of the ear of the patient through the second communicating path 23 that is relatively wide. In particular, in the case of an otolaryngology surgery, since a location and/or a condition of an eardrum may be checked by using a headlight worn by a medical staff, the surgery may be performed easily without using a microscope for intra-tympanic injection as in the related art.

Thereafter, as shown in FIG. 16, the first tip 1 may be inserted to the second communication path 23, and an eardrum may be accurately pierced by passing an injection needle through the first communication path 13. By coupling a first tip to a second tip, a medical staff may more accurately observe a condition of an ear and subsequently perform an accurate intra-tympanic injection.

The length S of the second tip 2 as described above may be equal to or greater than the length 1 of the first tip 1 described above. In other words, in a coupled state, the end portion 1-2 102 of the first tip 1 may meet the end portion 2-2 202 of the second tip 2, or the end portion 1-2 102 may be recessed from the end portion 2-2 202.

Meanwhile, the end portion 1-1 101 and the end portion 2-1 201 may coincide with each other when the first tip 1 and the second tip 2 are coupled to each other.

Figure 17:
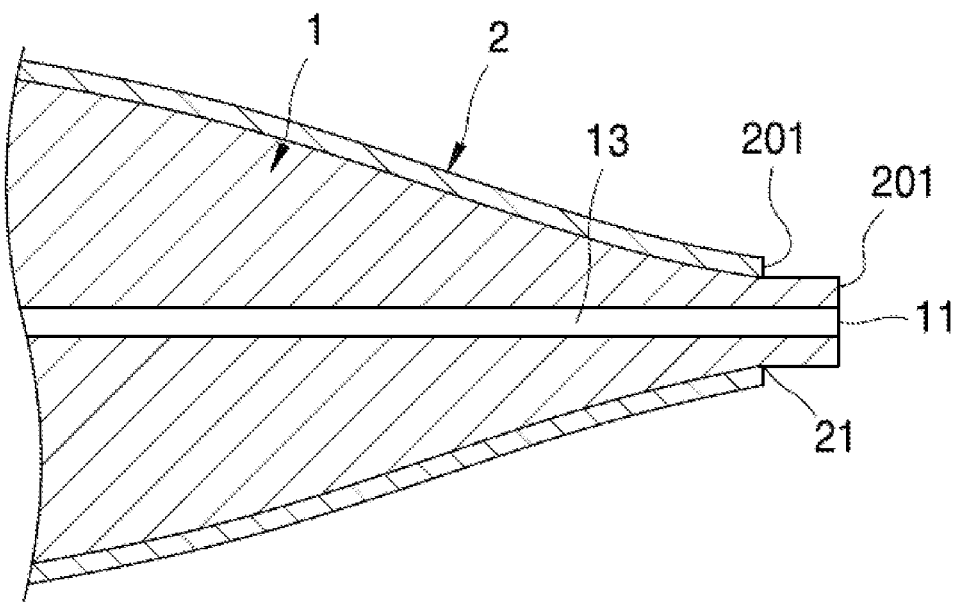
FIG. 17 is a cross-sectional view partially showing another embodiment in which a first tip for intra-tympanic injection and a second tip are coupled to each other.

However, the disclosure is not limited thereto, and, as shown in FIG. 17, the end portion 1-1 101 may protrude out of the opening 2-1 21. In this case, since the second tip 2 protrudes and extends toward an eardrum, the first tip 1 may be extended closer to the eardrum.

Figure 18:
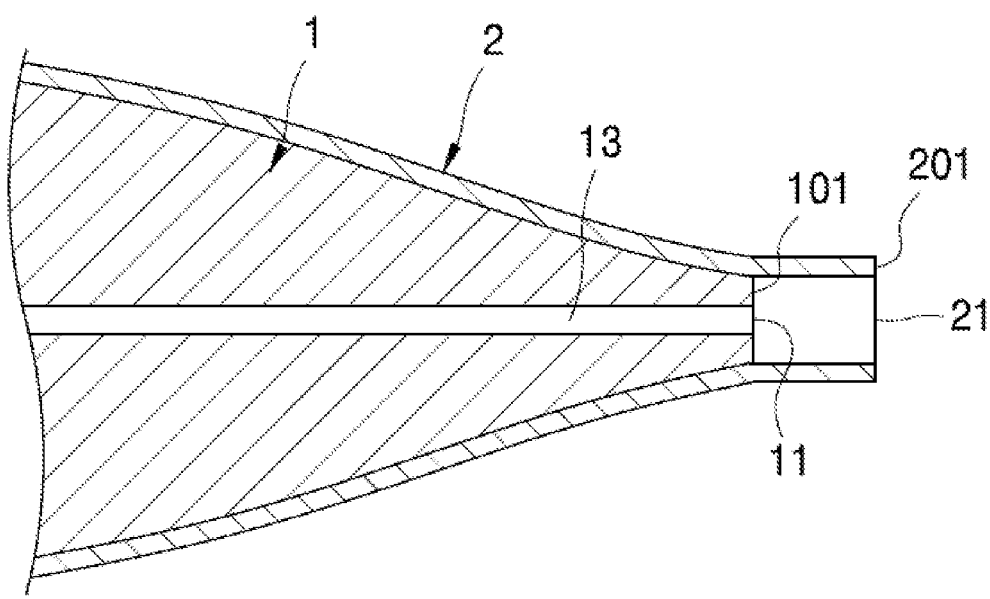
FIG. 18 is a cross-sectional view partially showing another embodiment in which a first tip for intra-tympanic injection and a second tip are coupled to each other.

In some embodiments, as shown in FIG. 18, the end portion 1-1 101 may be located inside the end portions 2-1 201 without protruding out of the opening 2-1 21. In this case, since an injection may be performed while the second tip 2 is located close to an eardrum, thereby preventing a patient from feeling irritation of the first tip 1 coming close to the eardrum.

Figure 19:
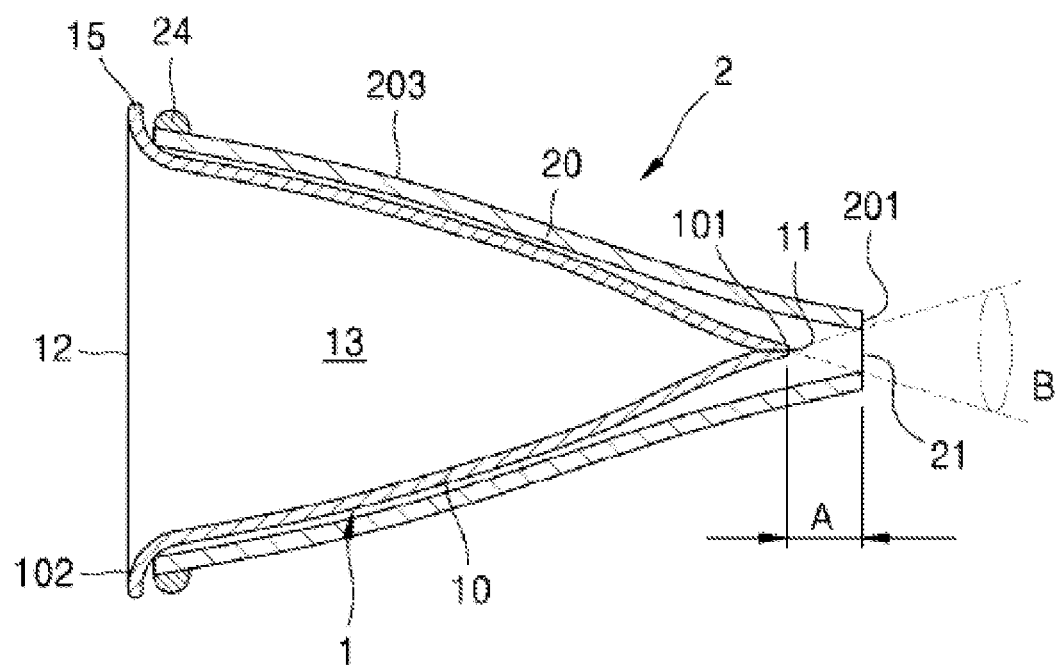
FIG. 19 is a cross-sectional view showing another embodiment in which a first tip for intra-tympanic injection and a second tip are coupled to each other.

FIG. 19 is a cross-sectional view showing another embodiment in which the first tip 1 for intra-tympanic injection and the second tip 2 are coupled to each other.

Referring to FIG. 19, the opening 1-1 11 formed in the first tip 1 is formed to have a size slightly larger than the diameter of an injection needle, which is large enough to allow an injection needle to pass therethrough, and the opening 1-2 12 may be formed to have a very large size. In this case, the first body 10 may be formed to have the same thickness from the opening 1-1 11 to the opening 1-2 12. Since the first tip 1 having such a structure allows an injection needle to change an angle within the range of an angle formed by the inner surface of the first body 10 constituting the first communicating path 13, the inner surface of the first body 10 may be designed to form an appropriate angle to allow the injection angle to pierce an eardrum without being shaken.

In some embodiments, when the end portion 1-1 101 and the end portion 2-1 201 are designed to be a predetermined distance A apart from each other in case where the first tip 1 as described above is coupled to the second tip 2 as shown in FIG. 19, an injection needle passed through the opening 1-1 11 passes through the opening 2-1 21, and thus an angle range in which the injection needle may move is narrowed. Therefore, the injection needle may pierce an eardrum only even when a practitioner carelessly performs an injection. Therefore, more accurate intra-tympanic injection may be performed.

As described above, when the first body 10 of the first tip 1 is formed to have the above-described structure, the first body 10 may be formed thinner, and thus the first tip 1 may be mass-produced more inexpensively.

The above-stated embodiments may be equally applied to all embodiments of the disclosure.

Conventionally, since it is necessary to check a location and/or a condition of an eardrum by using a microscope for an intra-tympanic injection, a surgery may only be performed on an otolaryngology chair adjacent to a microscope. Also, since a patient needs to be lie on a chair for 40 minutes or longer for a surgery, the corresponding chair may not be used for other diagnosis or treatment during the surgery, and the patient needs to lie on an uncomfortable chair for a long time.

According to the embodiments of the disclosure as described above, since a surgery may be performed while a patient is lying on a bed comfortably without using a microscope and/or an otolaryngology chair, equipment of a hospital may be easily utilized and the patient may receive the surgery in a comfortable state.

Also, in the case of performing an intra-tympanic injection by using only an auriscope tip as in the conventional intra-tympanic injection method, when a hand of a medical staff shakes during the intra-tympanic injection, an injection needle may be shaken and an eardrum may be minutely torn. Also, since a patient may move the head due to fear and pain during a surgery, an eardrum may be torn due to such a movement of the patient.

When an eardrum is torn, a fine hole formed in the eardrum by an injection needle may become larger, thereby causing an eardrum perforation that may cause hearing loss of the patient.

However, the disclosure may prevent an injection needle from being shaken due to shaking of a hand of a medical staff or a movement of a patient, thereby reducing the possibility of an eardrum perforation after a surgery.

While the disclosure has been particularly shown and described with reference to preferred embodiments thereof, It will be understood by those skilled in the art that various changes in form and details may be made therein without departing from the spirit and scope of the disclosure as defined by the appended claims. The preferred embodiments should be considered in descriptive sense only and not for purposes of limitation. In addition, individual embodiments described herein may be applied to other embodiments, and various combinations of all embodiments of the present specification are also included in the scope of the disclosure.

Therefore, the scope of the disclosure is defined not by the detailed description of the disclosure but by the appended claims, and all differences within the scope will be construed as being included in the disclosure.

INDUSTRIAL APPLICABILITY

The disclosure may provide a tip for intra-tympanic injection.

The invention claimed is:

1. A tip for intra-tympanic injection, the tip comprising:
a body having a first end portion and a second end portion, the first end portion having a cross-section smaller than that of the second end portion for being inserted into an external auditory meatus;
a first opening located at the first end portion of the body;
a second opening located at the second end portion of the body; and
a communicating path configured to penetrate through the body to connect the first opening and the second opening,
wherein the communicating path includes a cylindrical wall extending straight from the first opening,
wherein a diameter of the cylindrical wall is constant along a length of the cylindrical wall,
wherein the body comprises an outer casing and a filing portion located inside the outer casing, the communicating path being formed through the filing portion, and
wherein the filing portion comprises a material harder than that of the outer casing.

2. The tip of claim 1, wherein the outer casing is configured to have elasticity.

3. The tip of claim 1, further comprising a handle located outside the second end portion of the body.

4. The tip of claim 1,
wherein the communicating path comprises:
a first communicating path adjacent the first opening; and
a second communicating path connected to the first communicating path and adjacent to the second opening, and
a diameter of at least a portion of the second communicating path is greater than a diameter of the first communicating path.

5. The tip of claim 1, wherein the body has a curved surface from the first end portion toward the second end portion.

6. The tip of claim 1, wherein a diameter of the first opening is smaller than a diameter of the second opening.

7. The tip of claim 1, wherein the communicating path comprises a portion formed in a linear shape.

8. A tip for intra-tympanic injection, the tip comprising:
a first tip; and
a second tip configured to be inserted into an external auditory meatus, the first tip being configured to be inserted into the second tip,
wherein the first tip comprises:
a body configured to be at least partially in close contact with an inner surface of the second tip; and
a communicating path configured to penetrate through the body,
wherein the communicating path includes a cylindrical wall extending straight from a first opening of the body, and
wherein a diameter of the cylindrical wall is constant along a length of the cylindrical wall.

9. The tip of claim 8,
wherein the communicating path comprises:
a first communicating path adjacent the first opening; and
a second communicating path connected to the first communicating path and adjacent to a second opening of the body, and
a diameter of at least a portion of the second communicating path is greater than a diameter of the first communicating path.

10. The tip of claim 8, wherein the body has a curved surface from the first end portion toward the second end portion.

11. The tip of claim 8, wherein a diameter of the first opening is smaller than a diameter of the second opening.

12. The tip of claim 8, wherein the communicating path comprises a portion formed in a linear shape.

* * * * *